United States Patent [19]
Andersen et al.

[11] Patent Number: 5,952,352
[45] Date of Patent: Sep. 14, 1999

[54] HETEROCYCLIC COMPOUNDS

[75] Inventors: Knud Erik Andersen, Smørum; Uffe Bang Olsen, Vallensbæk; Henrik Sune Andersen, København; Rolf Hohlweg, Kvistgaard; Tine Krogh Jørgenen, Herlev; Peter Madsen, Bagsværd; Zdenek Polivka, Prague; Alexandra Silhánková, Prague; Karel Sindelár, Prague, all of Denmark

[73] Assignee: Novo Nordisk A/S, Bagsvaerd, Denmark

[21] Appl. No.: 08/942,018

[22] Filed: Oct. 1, 1997

Related U.S. Application Data

[63] Continuation of application No. PCT/DK96/00151, Apr. 1, 1996.

[30] Foreign Application Priority Data

Apr. 7, 1995 [DK] Denmark ............................... 0417/95

[51] Int. Cl.$^6$ ................................................ A61R 31/445
[52] U.S. Cl. ........................ 514/321; 514/338; 546/197; 546/281.7
[58] Field of Search ................. 546/197, 281.7; 514/321, 338

[56] References Cited

U.S. PATENT DOCUMENTS

| | | | |
|---|---|---|---|
| 4,994,463 | 2/1991 | Oshima et al. | 514/253 |
| 5,668,129 | 9/1997 | Andersen et al. | 514/183 |
| 5,698,551 | 12/1997 | Jorgensen et al. | 514/217 |
| 5,721,260 | 2/1998 | Hohlweg et al. | 514/428 |
| 5,753,678 | 5/1998 | Hohlweg et al. | 514/321 |

FOREIGN PATENT DOCUMENTS

| | | |
|---|---|---|
| 0 221 572 | 5/1987 | European Pat. Off. . |
| 1176173 | 1/1979 | United Kingdom . |

OTHER PUBLICATIONS

Dostert et al, Chem. Abstracts, vol. 77, No. 19,451j, 1972.

Chem. Abstracts, vol. 115, No. 255,994n, 1991.

Pavia et al, Chem. Abstracts, vol. 107, No. 1 '34,212g, 1987.

Chemical Abstracts, vol. 118, No. 1, p. 726—The Abstract No. 6834b.

Falch et al., Drug Design and Delivery, vol. 4, pp. 205–215 (1989).

*Primary Examiner*—James H. Reamer
*Attorney, Agent, or Firm*—Steve T. Zelson; Carol E. Rozek

[57] ABSTRACT

The present invention relates to novel N-substituted azaheterocyclic carboxylic acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation.

11 Claims, No Drawings

HETEROCYCLIC COMPOUNDS

This application is a continuation of PCT/DK96/00151 filed Apr. 1, 1996 and claims priority under 35 U.S.C. 119 of Danish application serial no. 0417/95 filed Apr. 7, 1995, the contents of which are fully incorporated herein by reference.

FIELD OF THE INVENTION

The present invention relates to novel N-substituted aza-heterocyclic carboxylic acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation. The invention also relates to the use of the present compounds for the treatment of insulin resistance in non-insulin-dependent diabetes mellitus (NIDDM) or aging, the present compounds knowing to interfere with neuropeptide containing C-fibres and hence inhibit the secretion and circulation of insulin antagonizing peptides like CGRP or amylin.

BACKGROUND OF THE INVENTION

The nervous system exerts a profound effect on the inflammatory response. Antidromic stimulation of sensory nerves results in localized vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity, may be useful in treatment of, for example arthritis, dermatitis, rhinitis, asthma, cystitis, gingivitis, thrombophelitis, glaucoma, gastro-intestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or aging-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or aging.

In U.S. Pat. No. 4,383,999 and U.S. Pat. No. 4,514,414 and in EP 236342 as well as in EP 231996 some derivatives of N-(4,4-disubstituted-3-butenyl)-azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221 572 claims that 1-aryloxyalkyl-pyridine-3-carboxylic acids are inhibitors of GABA uptake.

DESCRIPTION OF THE INVENTION

The present invention relates to novel N-substituted aza-heterocyclic carboxylic acids and esters thereof of formula I

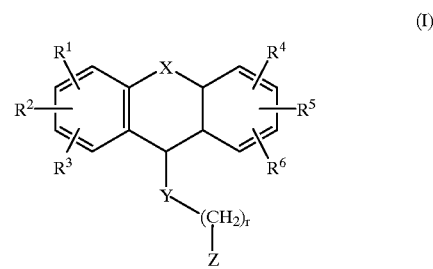

wherein $R^1$, $R^2$, $R^3$, $R^4$, $R^5$ and $R^6$ independently are hydrogen, halogen, trifluoromethyl, hydroxy, $C_{1-6}$-alkyl, $C_{1-6}$-alkoxy, $-NR^7R^8$ or $-SO_2NR^7R^8$ wherein
$R^7$ and $R^8$ independently are hydrogen or $C_{1-6}$-alkyl; and
X is completion of an optional bond, $-CH_2-$, $-CH_2CH_2-$, $-CH=CH-$, $-O-$, $-S(O)_z-$ wherein z is 0, 1 or 2, or $-N(R^9)-$ wherein $R^9$ is hydrogen or $C_{1-6}$-alkyl; and
Y is $-O-$, $S(O)_q-$ wherein q is 0, 1 or 2, or $-N(R^{10})-$ wherein $R^{10}$ is hydrogen or $C_{1-6}$-alkyl; and
r is 1, 2, 3 or 4; and
Z is selected from

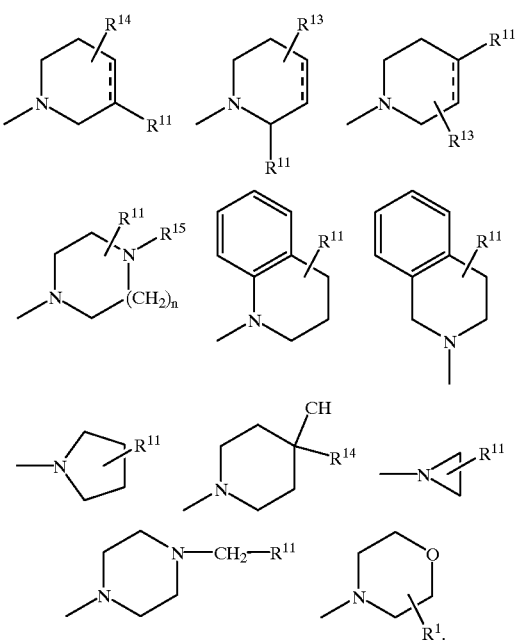

wherein n is 1 or 2; and
$R^{11}$ is $-(CH_2)_mOH$ or $-(CH_2)_tCOR^{12}$ wherein m is 0, 1, 2, 3, 4, 5 or 6 and t is 0 or 1 and wherein $R^{12}$ is $-OH$, $-NH_2$, $-NHOH$ or $C_{1-6}$-alkoxy; and
$R^{13}$ is hydrogen, halogen, trifluoromethyl, hydroxy, $C_{1-6}$-alkyl or $C_{1-6}$-alkoxy; and $R^{14}$ is hydrogen, $C_{1-6}$-alkyl, $C_{1-6}$-alkoxy or phenyl optionally substituted with halogen, trifluoromethyl, hydroxy, $C_{1-6}$-alkyl or $C_{1-6}$-alkoxy; and $R^{15}$ is hydrogen or $C_{1-6}$-alkyl; and ... is optionally a single bond or a double bond; or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated-ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are hereby incorporated by reference.

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "halogen" means fluorine, chlorine, bromine or iodine.

Illustrative examples of compounds encompassed by the present invention include:

1-(2-(10,11-Dihydro-5H-dibenzo[a,d]cyclohepten-5-yloxy) ethyl)-3-piperidinecarboxamide;
1-(2-(10,11-Dihydro-5H-dibenzo[a,d]cyclohepten-5-yloxy) ethyl)-4-piperidinecarboxylic acid;
1-(2-(10,11-Dihydro-5H-dibenzo[a,d]cyclohepten-5-yloxy) ethyl)-2-piperidinecarboxylic acid;
(1-(2-(10,11-Dihydro-5H-dibenzo[a,d]cyclohepten-5-yloxy)ethyl)piperidin-3-yl)methanol;
4-(4-Chlorophenyl)-1-(2-(10,11-Dihydro-5H-dibenzo[a,d] cyclohepten-5-yloxy)-ethyl)-4-piperidinol;
4-(2-(10,11-Dihydro-5H-dibenzo[a,d]cyclohepten-5-yloxy) ethyl)-4-piperazinecarboxylic acid;
(2S,4R)-1-(2-(10,11-Dihydro-5H-dibenzo[a,d]cyclohepten-5-yloxy)ethyl)-4-hydroxy-2-pyrrolidinecarboxylic acid;
4-(2-(10,11-Dihydro-5H-dibenzo[a,d]cyclohepten-5-yloxy) ethyl)-2-morpholinecarboxylic acid;
1-(2-(10,11-Dihydro-5H-dibenzo[a,d]cyclohepten-5-yloxy) ethyl)-2-aziridinecarboxylic acid;
2-(2-(10,11-Dihydro-5H-dibenzo[a,d]cyclohepten-5-yloxy) ethyl)-1,2,3,4-tetrahydro-4-isoquinolinecarboxylic acid;
1-(2-(10,11-Dihydro-5H-dibenzo[a,d]cyclohepten-5-yloxy) ethyl)-4-methyl-1,4-diazepane-6-carboxylic acid;
2-(2-(10,11-Dihydro-5H-dibenzo[a,d]cyclohepten-5-yloxy) ethyl)-1,2,3,4-tetrahydro-3-isoquinolinecarboxylic acid;
1-(2-(10,11-Dihydro-5H-dibenzo[a,d]cyclohepten-5-yloxy) ethyl)-3-piperidinecarboxylic acid hydroxamide;
(4-(2-(10,11-Dihydro-5H-dibenzo[a,d]cyclohepten-5-yloxy ethyl)piperazin-1-yl)acetic acid;
or a pharmaceutically acceptable salt thereof.

As used herein, the term "patient" includes any mammal which could benefit from treatment of neurogenic pain or inflammation or insulin resistance in NIDDM. The term particularly refers to a human patient, but is not intended to be so limited.

It has been demonstrated that the novel compounds of formula I inhibit neurogenic inflammation which involves the release of neuropeptides from peripheral and central endings of sensory C-fibres. Experimentally this can be demonstrated in animal models of formalin induced pain or paw oedema (Wheeler and Cowan, Agents Actions 1991, 34, 264–269) in which the novel compounds of formula I exhibit a potent inhibitory effect. Compounds of formula I may be used to treat all painful, hyperalgesic and/or inflammatory conditions in which C-fibers play a pathophysiological role by eliciting neurogenic pain or inflammation, i.e.:

Acutely painful conditions exemplified by migraine, postoperative pain, burns, bruises, post-herpetic pain (Zoster) and pain as it is generally associated with acute inflammation; chronic, painful and/or inflammatory conditions exemplified by various types of neuropathy (diabetic, posttraumatic, toxic), neuralgia, rheumatoid arthritis, spondylitis, gout, inflammatory bowel disease, prostatitis, cancer pain, chronic headache, coughing, asthma, chronic pancreatitis, inflammatory skin disease including psoriasis and autoimmune dermatoses, osteoporotic pain.

Further, it has been demonstrated that the compounds of general formula I improves the glucose tolerance in diabetic ob/ob mice and that this may result from the reduced release of CGRP from peripheral nervous endings. Hence the compounds of general formula I may be used in the treatment of NIDDM as well as aging-associated obesity. Experimentally this has been demonstrated by the subcutaneous administration of glucose into ob/ob mice with or without previous oral treatment with a compound of general formula I.

The compounds of formula I may be prepared by the following method:

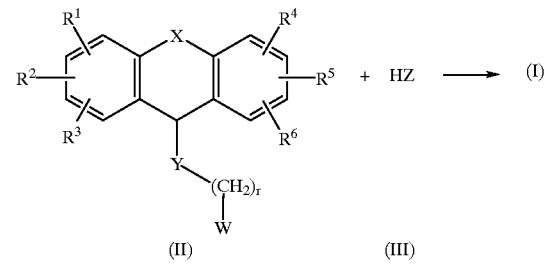

A compound of formula II wherein $R^1$, $R^2$, $R^3$, $R^4$, $R^5$, $R^6$, X, Y and r are as defined above and W is a suitable leaving group such as halogen, p-toluene sulphonate or mesylate may be reacted with an azaheterocyclic compound of formula III wherein Z is as defined above. This alkylation reaction may be carried out in a solvent such as acetone, dibutylether, 2-butanone, methyl ethyl ketone, ethyl acetate, tetrahydrofuran (THF) or toluene in the presence of a base e.g. sodium hydride and a catalyst, e.g. an alkali metal iodide at a temperature up to reflux temperature for the solvent used for e.g. 1 to 120 h. If esters have been prepared in which $R^{12}$ is alkoxy, compounds of formula I wherein $R^{12}$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

Pharmacological Methods

Release of neuropeptides from pheriphal and central endings of sensory C-fibers

Values for in vivo inhibition of formalin induced pain or oedema for the compounds of the present invention were assessed in mice essentially by the method of Wheeler-Aceto and Cowan (Agents Action 1991, 34, 265–269).

About 20 g NMRI female mice were injected 20 $\mu$l 1% formalin into the left hind paw. The animals were then placed on a heated (31° C.) table, and the pain response was scored. After 1 h they were killed and bled. Left and right hind paws were removed and the weight difference between the paws was used as indication of the oedema response of the formalin injected paw.

Reduced release of CGRP from pheriphal nervous endings ob/ob female mice, 16 weeks of age, where injected glucose (2g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in a pharmaceutically acceptable acid addition salt form or where possible as a metal or a lower alkylammonium salt. Such salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispensed in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC approx. | 9 mg |
| *Mywacette ® 9-40 T approx. | 0.9 mg |

*Acylated monoglyceride used as plasticizer for film coating.

The route of administration may be any route which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

EXAMPLES

The process for preparing compounds of formula I and preparations containing them is further illustrated in the following examples, which, however, are not to be construed as limiting.

Hereinafter, TLC is thin layer chromatography and THF is tetrahydrofuran, $CDCl_3$ is deuterio chloroform and $DMSO-d_6$ is hexadeuterio dimethylsulfoxide. The structures of the compounds are confirmed by either elemental analysis or NMR, where peaks assigned to characteristic protons in the title compounds are presented where appropriate. $^1$H-NMR shifts ($\epsilon_H$) are given in parts per million (ppm). M.p. is melting point and is given in °C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

1-(2-(10,11-Dihydro-5H-dibenzo[a,d]cyclohepten-5-yloxy)-1-ethyl)-4-piperidine-carboxylic acid hydrochloride

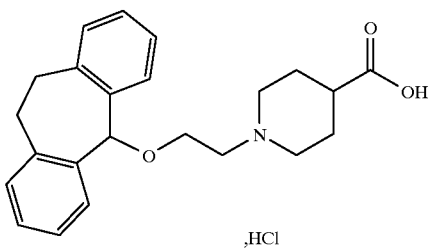

A mixture of 10,11-dihydro-5H-dibenzo[a,d]cyclohepten-5-ol (10.0 g, 0.047 mol), 2-bromoethanol (8.6 g, 0.069 mol) and concentrated sulphuric acid (1.4 ml) in benzene (120 ml) was stirred for 0.5 h at room temperature. After cooling (water/ice), crude 5-(2-bromoethoxy-10,11-dihydro-5H-dibenzo[a,d]cyclohepten was filtered off, washed with petroleum ether and dried. This afforded 10.7 g (72%), which was used without purification for further reaction.

M.p. 62–70° C.

A mixture of 5-(2-bromoethoxy)-10,11-dihydro-5H-dibenzo[a,d]cycloheptene (9.5 g, 0.03 mol), ethyl 4-piperidinecarboxylate (4.7 g, 0.03 mol), potassium carbonate (8.1 g, 0.06 mol) and dimethylsulfoxide (120 ml) was stirred on a water bath at 40–50° C. for 4 h. The mixture was cooled, filtered and the solid was washed with dimethylsulfoxide (10 ml). The combined filtrates were diluted with water (720 ml) and extracted with diethyl ether (2×200 ml). The ether extract was washed with water, dried (MgSO$_4$), and the solvent was evaporated under vacuum. The residue was dissolved in 2-propanol, and a hot solution of oxalic acid (4.0 g) in 2-propanol was added. After cooling, crystals of ethyl 1-(10,11dihydro-5H-dibenzo[a,d]cyclohepten-5-yloxy)-1-ethyl-4-piperidinecarboxylate hydrogen oxalate precipitated. This afforded after filtration and drying 8.3 g (57%), which was used for further reaction without purification.

The above oxalate suspension (7.3 g, 0.015 mol) in water was made alkaline with a 25% ammonia solution and extracted with diethyl ether (2×100 ml). The organic layer was washed with water (2×50 ml), dried (MgSO$_4$) and evaporated in vacuum. This afforded 5.7 g (96%) of free ethyl ester as an oil.

A mixture of the above ester 2.01 g (0.005 mol), 2.4 ml 20% aqueous sodium hydroxide and ethanol (15 ml) was stirred at room temperature for 4 h and overnight. Dichloromethane (250 ml) was added, and under magnetic stirring and cooling (water/ice bath), ~2.5 N HCl was carefully added dropwise to pH 1. The water layer was separated, and the organic layer was dried (MgSO$_4$) and evaporated under vacuum. The solid residue was re-evaporated twice with acetone. This afforded 1.68 g (83%) the title compound after crystallisation from a mixture of ethanol and ether. Dichloromethane, which was present in the crystalline sample was removed under vacuum at elevated temperature.

M.p. 192–194° C.

$^1$H NMR (DMSO-d$_6$): 7.42 (bd, 2H); 7.19 (m, 6H); 5.62 (s, 1H); 3.83 (t, 2H); 3.28 (t, 1H); 4.96 (d, 1H); 2.53 (m, 1H); 3.37 (m, 6H); 3.00 (m, 4H); 1.99 (m, 4H).

We claim:
1. A compound of formula I

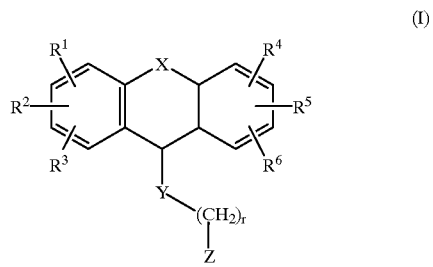

wherein $R^1$, $R^2$, $R^3$, $R^4$, $R^5$ and $R^6$ independently are hydrogen, halogen, trifluoromethyl, hydroxy, $C_{1-6}$-alkyl, $C_{1-6}$-alkoxy, —NR$^7$R$^3$ or —SO$_2$NR$^7$R$^8$ wherein $R^7$ and $R^8$ independently are hydrogen or $C_{1-6}$-alkyl; and X is completion of an optional bond, —CH$_2$—, —CH$_2$CH$_2$—, —CH=CH—, —O—, —S(O)$_z$— wherein z is 0, 1 or 2, or —N(R$^9$)— wherein R$^9$ is hydrogen or $C_{1-6}$-alkyl; and Y is —O—, —S(O)$_q$— wherein q is 0, 1 or 2, or —N(R$^{10}$)— wherein R$^{10}$ is hydrogen or $C_{1-6}$-alkyl; and r is 1, 2, 3 or 4; and Z is selected from

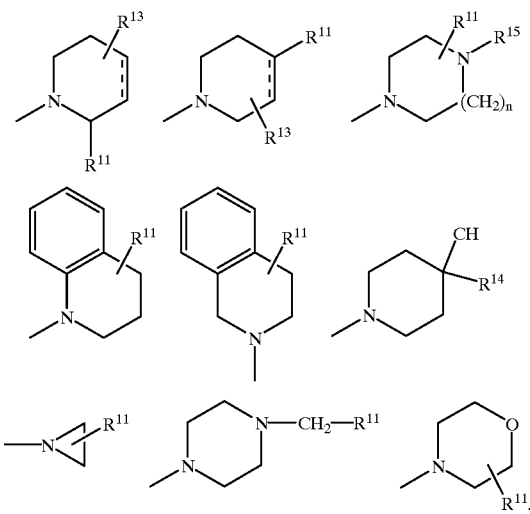

wherein n is 1 or 2; and $R^{11}$ is —(CH$_2$)$_m$OH or —(CH$_2$)$_t$COR$^{12}$ wherein m is 0, 1, 2, 3, 4, 5 or 6 and t is 0 or 1 and wherein $R^{12}$ is —OH, —NH$_2$, —NHOH or $C_{1-6}$-alkoxy; and $R^{13}$ is hydrogen, halogen, trifluoromethyl, hydroxy, $C_{1-6}$-alkyl or $C_{1-6}$-alkoxy; and $R^{14}$ is hydrogen, $C_{1-6}$-alkyl, $C_{1-6}$-alkoxy or phenyl optionally substituted with halogen, trifluoromethyl, hydroxy, $C_{1-6}$-alkyl or $C_{1-6}$-alkoxy; and $R^{15}$ is hydrogen or $C_{1-6}$-alkyl; and ... is optionally a single bond or a double bond;

or a pharmaceutically acceptable salt thereof.

2. A compound according to claim 1 selected from the following:

1-(2-(10,11-Dihydro-5H-dibenzo[a,d]cyclohepten-5-yloxy) ethyl)-4-piperidinecarboxylic acid;

1-(2-(10,11-Dihydro-5H-dibenzo[a,d]cyclohepten-5-yloxy) ethyl)-2-piperidinecarboxylic acid;

4-(4-Chlorophenyl)-1-(2-(10,11-Dihydro-5H-dibenzo[a,d]cyclohepten-5-yloxy)ethyl)-4-piperidinol;

4-(2-(10,11-Dihydro-5H-dibenzo[a,d]cyclohepten-5-yloxy)ethyl)-4-piperazinecarboxylic acid;

4-(2-(10,11-Dihydro-5H-dibenzo[a,d]cyclohepten-5-yloxy)ethyl)-2-morpholinecarboxylic acid;

1-(2-(10,11-Dihydro-5H-dibenzo[a,d]cyclohepten-5-yloxy)ethyl)-2-aziridinecarboxylic acid;

2-(2-(10,11-Dihydro-5H-dibenzo[a,d]cyclohepten-5-yloxy)ethyl)-1,2,3,4-tetrahydro-4-isoquinolinecarboxylic acid;

1-(2-(10,11-Dihydro-5H-dibenzo[a,d]cyclohepten-5-yloxy)ethyl)-4-methyl-1,4-diazepane-6-carboxylic acid;

2-(2-(10,11-Dihydro-5H-dibenzo[a,d]cyclohepten-5-yloxy)ethyl)-1,2,3,4-tetrahydro-3-isoquinolinecarboxylic acid;

(4-(2-(10,11-Dihydro-5H-dibenzo[a,d]cyclohepten-5-yloxy)ethyl)piperazin-1-yl)acetic acid;

or a pharmaceutically acceptable salt thereof.

3. A pharmaceutical composition comprising as an active component a compound of claim 1 together with a pharmaceutically acceptable carrier or diluent.

4. The pharmaceutical composition of claim 3 comprising between 0.5 mg and 1000 mg of the compound per unit dose.

5. A method of treating neurogenic pain or inflammation comprising administering to a subject in need thereof an effective amount of a compound of claim 1.

6. A method of treating neurogenic pain or inflammation comprising administering to a subject in need thereof a pharmaceutical composition of claim 3.

7. The compound according to claim 1 in which the compound is 1-(2-(10,11-dihydro-5H-dibenzo[a,d]cyclohepten-5-yloxy)ethyl)-4-piperidinecarboxylic acid.

8. A method of treating neurogenic pain or inflammation associated with neuropathy, rheumatoid arthritis or migraine, comprising administering to a subject in need thereof an effective amount of a compound of claim 1.

9. A method of treating neurogenic pain or inflammation associated with neuropathy, rheumatoid arthritis or migraine, comprising administering to a subject in need thereof a pharmaceutical composition of claim 3.

10. A method of treating non-insulin-dependent diabetes mellitus (NIDDM) comprising administering to a subject in need thereof an effective amount of a compound of claim 1.

11. A method of treating non-insulin-dependent diabetes mellitus (NIDDM) comprising administering to a subject in need thereof a pharmaceutical composition of claim 3.

\* \* \* \* \*